United States Patent
Saito et al.

(10) Patent No.: US 10,080,623 B2
(45) Date of Patent: Sep. 25, 2018

(54) VISIBLE LIGHT PROJECTION DEVICE FOR SURGERY TO PROJECT IMAGES ON A PATIENT

(71) Applicant: Panasonic Intellectual Property Management Co., Ltd., Osaka (JP)

(72) Inventors: Tomoyuki Saito, Kyoto (JP); Etsuro Hatano, Kyoto (JP); Takashi Nitta, Kyoto (JP); Satoru Seo, Kyoto (JP); Hisashi Nishida, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/718,487

(22) Filed: Sep. 28, 2017

(65) Prior Publication Data
US 2018/0014901 A1 Jan. 18, 2018

Related U.S. Application Data

(63) Continuation of application No. PCT/JP2015/004946, filed on Sep. 29, 2015.

(30) Foreign Application Priority Data

Mar. 31, 2015 (JP) .................... 2015-073309

(51) Int. Cl.
*A61B 5/00* (2006.01)
*A61B 90/00* (2016.01)
(Continued)

(52) U.S. Cl.
CPC ............ *A61B 90/36* (2016.02); *A61B 5/0071* (2013.01); *A61B 34/20* (2016.02); *A61B 90/00* (2016.02);
(Continued)

(58) Field of Classification Search
CPC . A61B 90/36; A61B 5/0071; A61B 2090/373; A61B 2090/366; A61B 5/4887–5/489
See application file for complete search history.

(56) References Cited

U.S. PATENT DOCUMENTS

| 5,772,593 A | 6/1998 | Hakamata |
| 8,473,035 B2 * | 6/2013 | Frangioni .............. A61B 5/415 600/476 |

(Continued)

FOREIGN PATENT DOCUMENTS

| JP | 9-24053 | 1/1997 |
| JP | 2012-23492 | 2/2012 |

(Continued)

OTHER PUBLICATIONS

International Preliminary Report on Patentability issued in International Application No. PCT/JP2015/004926 dated Oct. 12, 2017.

(Continued)

*Primary Examiner* — Serkan Akar
(74) *Attorney, Agent, or Firm* — Wenderoth, Lind & Ponack, L.L.P.

(57) ABSTRACT

A visible light projection device includes a detecting unit that detects a first region emitting non-visible light, a projecting unit that performs projection using visible light onto a second region including the detected first region, and a control unit that controls the projecting unit to perform projection with a color selected by an operator. When a first color is selected as a color of visible light projected by the projecting unit onto a region other than the first region, the control unit informs the operator of first options to allow a color of visible light projected onto the first region to be selected from the first options. When a second color different from the first color is selected, the control unit informs the operator of second options to allow a color of visible light projected onto the first region to be selectable from the second options.

4 Claims, 6 Drawing Sheets

(51) Int. Cl.
*A61B 34/20* (2016.01)
*A61B 17/00* (2006.01)
*A61B 34/00* (2016.01)
*A61B 90/30* (2016.01)

(52) U.S. Cl.
CPC ............ *A61B 34/25* (2016.02); *A61B 90/361* (2016.02); *A61B 2017/00778* (2013.01); *A61B 2034/2057* (2016.02); *A61B 2034/2065* (2016.02); *A61B 2090/304* (2016.02); *A61B 2090/366* (2016.02); *A61B 2090/373* (2016.02); *A61B 2505/05* (2013.01)

(56) References Cited

U.S. PATENT DOCUMENTS

| | | | |
|---|---|---|---|
| 2002/0105505 A1* | 8/2002 | Sendai | A61B 5/0071 345/204 |
| 2005/0195587 A1 | 9/2005 | Moctezuma De La Barrera et al. | |
| 2007/0203413 A1* | 8/2007 | Frangioni | A61B 5/415 600/478 |
| 2012/0016230 A1* | 1/2012 | Kishima | A61B 1/00186 600/425 |
| 2014/0039309 A1* | 2/2014 | Harris | A61B 5/7282 600/431 |
| 2014/0187931 A1* | 7/2014 | Wood | A61B 5/0071 600/431 |
| 2015/0177598 A1 | 6/2015 | Mima et al. | |
| 2015/0181153 A1 | 6/2015 | Mima et al. | |

FOREIGN PATENT DOCUMENTS

| | | |
|---|---|---|
| WO | 2009/120228 | 10/2009 |
| WO | 2015/001807 | 1/2015 |

OTHER PUBLICATIONS

International Search Report issued in International Application No. PCT/JP2015/004946 dated Dec. 25, 2015, with English translation.

* cited by examiner

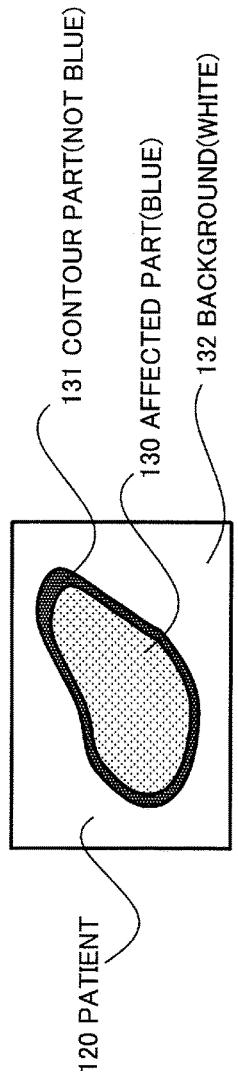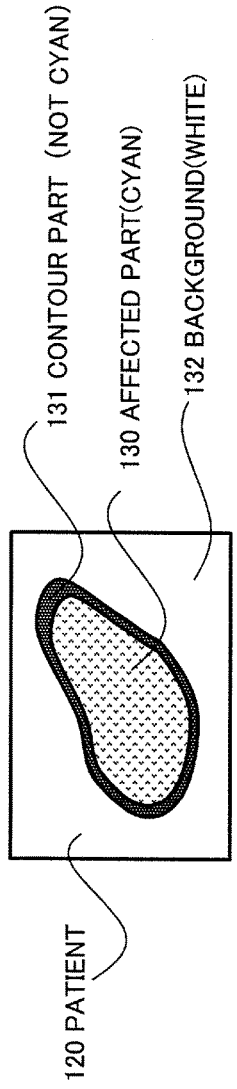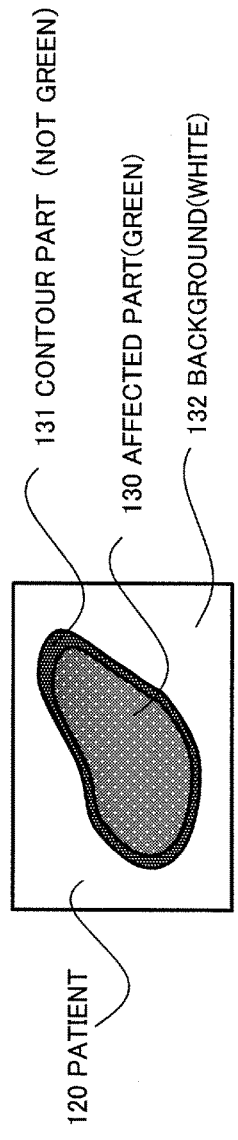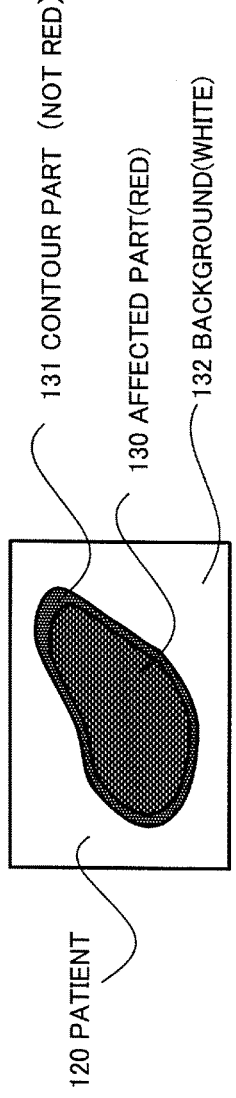

*SATURATION C4 > C3 > C2 > C1

VISIBLE LIGHT PROJECTION DEVICE FOR SURGERY TO PROJECT IMAGES ON A PATIENT

BACKGROUND

1. Technical Field

The present disclosure relates to a visible light projection device that projects visible light onto a region where a non-visible light emission is detected.

2. Related Art

Japanese laid-open Patent publication No. JP H09-024053 A discloses a surgical operation support system which outputs image data representing an affected part of a living body undergoing a surgical operation with a fluorescent image capturing device, and reproduces an image from the image data with an image projection device to display it on an actual affected part. A substance which fluoresces upon receiving irradiation of light of a predetermined wavelenyLh is administered previously to the affected part of the living body.

That is, this system displays a fluorescence image of a fluorescing affected part on the actual affected part, to support confirmation of a lesioned part.

SUMMARY

An object of the present disclosure is to provide a more usable visible light projection device.

A visible light projection device according to the present disclosure includes a detecting unit that detects a first region emitting non-visible light, a projecting unit that performs projection using visible light onto a second region including the first region detected by the detecting unit, and a control unit that controls the projecting unit to perform projection with a color selected by an operator. When a first color is selected as a color of visible light projected by the projecting unit onto a region other than the first region within the second region, the control unit informs the operator of a color of visible light projected onto the first region by the projecting unit to be selectable from first options. On the other hand, when a second color different from the first color is selected as a color of visible light projected by the projecting unit onto a region other than the first region within the second region, the control unit informs the operator of a color of visible light projected onto the first region by the projecting unit to be selectable from second options different from a combination of candidates included in the first options.

More preferably, the control unit prohibits selection of a color selected by the operator as a color of visible light projected onto the first region by the projecting unit, from options of the color of visible light projected onto a contour portion of the first region by the projecting unit.

More preferably, when making the projecting unit perform projection onto the first region using color visible light with multi-grayscale levels according to an intensity of non-visible light from portions composing the first region detected by the detecting unit, the control unit varies saturation of the color of visible light projected by the projecting unit, according to a grayscale of the visible light.

The present disclosure can provide a more usable visible light projection device.

BRIEF DESCRIPTION OF DRAWINGS

FIGS. 5A-5D are views each depicting a projection video in a case where the grayscale level is limited to 2 levels with a white background color.

DETAILED DESCRIPTION OF EMBODIMENT

Embodiments will now be described in detail with proper reference to the drawings. It is to be noted that unnecessarily detailed description may be omitted. For example, detailed description of already well-known matters or repeated description of substantially the same configurations may be omitted. This is to prevent the following description from becoming unnecessarily redundant, to facilitate the understanding of the user.

The applicant provides the accompanying drawings and the following description so that those skilled in the art can fully understand this disclosure, but does not intend to limit the subject matter of claims thereby.

First Embodiment

1. Overview of Surgery Support System

Hereinafter, by way of example, a first embodiment will be described in which a projection system of the present disclosure is applied to surgery support in hospital. The projection system applied to the surgery support in hospital is referred to as a surgery support system 100.

Figure 1:
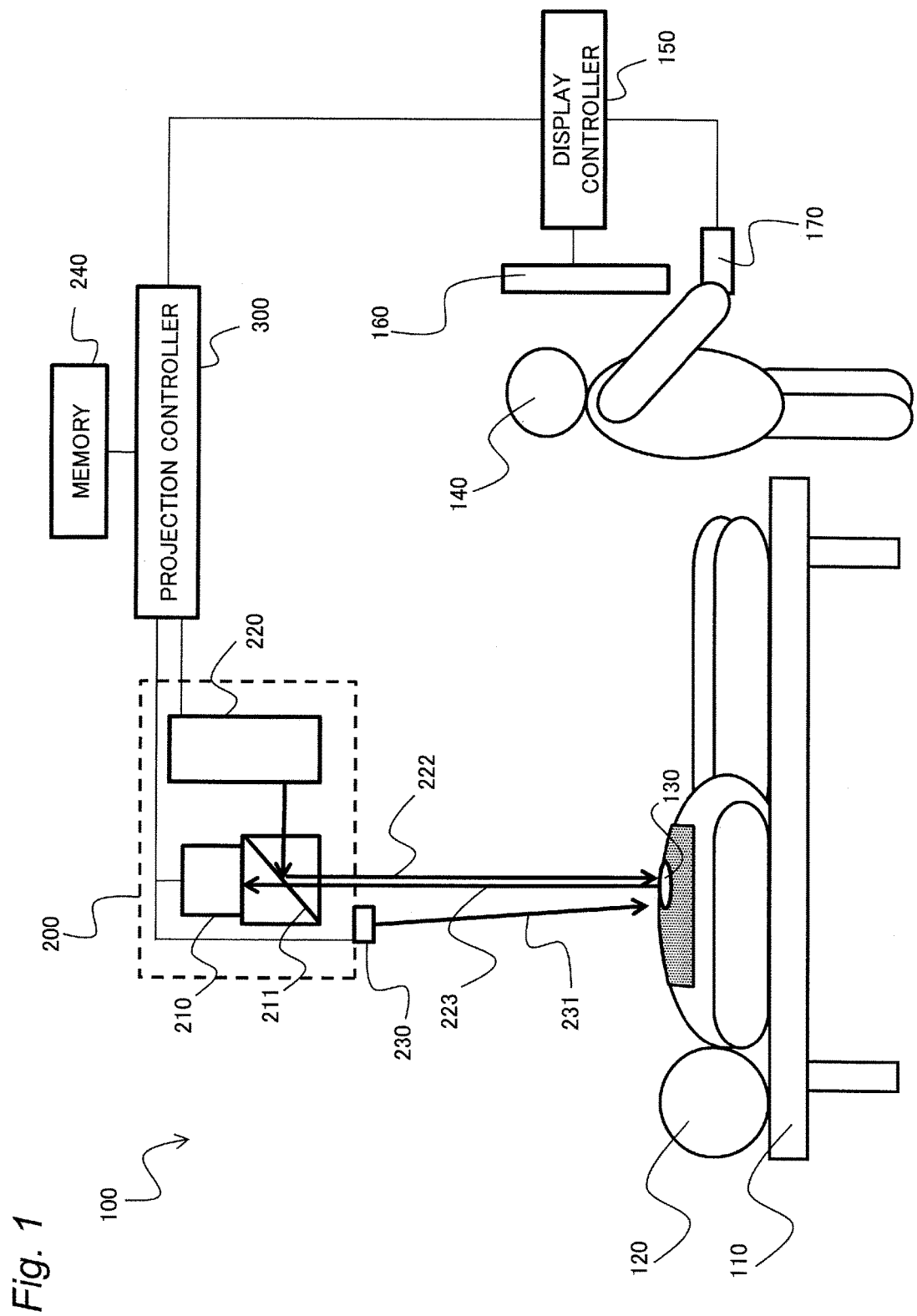
FIG. 1 is a diagram explaining a configuration of a surgery support system 100.

Referring to FIG. 1, an overview of the surgery support system 100 accordi ng to the first embodiment will first be described. FIG. 1 is a diagram explaining a configuration of the surgery support system 100. As depicted in FIG. 1, the surgery support system 100 is arranged such that an imaging and irradiating device 200 is positioned above a patient 120 lying on an operating table 110.

In utilizing the surgery support system 100, a light-sensitive substance is delivered into blood etc. of the patent 120 undergoing surgery. The light-sensitive substance is a substance that fluoresces when receiving excitation light. In the first embodiment, a case will be described using indocyanine green (hereinafter, abbreviated as "ICG") as an example of the light-sensitive substance. ICG has medical approval and is a reagent available for a human body. When delivered into the blood, ICG is accumulated in an affected part 130 where blood or lymph flow stagnates. When irradiated with infrared excitation light of approx. 800 nm, ICG emits infrared fluorescent light of approx. 850 nm in peak wavelength. Accordingly, it becomes possible to specify a region of the affected part 130 if a region (ICG light-emitting region) emitting infrared fluorescent light can be detected.

The surgery support system 100 is a system specifying a region of the affected part 130 by detecting a region from which ICG emits infrared fluorescent light. The surgery support system 100 projects visible light onto the specified region of the affected part 130 in order to allow a doctor to visually recognize the specified region of the affected part 130. This enables the surgery support system 100 to support the doctor's specification of the region of the affected part 130 when surgery is performed on the affected part 130.

2. Configuration of Surgery Support System

Details of the configuration of the surgery support system 100 will then be described with reference to FIG. 1. The surgery support system 100 is disposed and used in an operating room of a hospital. The surgery support system 100 includes mainly the imaging and irradiating device 200, a projection controller 300, a memory 240, and an infrared excitation light source 230. The surgery support system 100 further includes a display controller 150, a display 160, and a mouse 170 to receive various setting operations from the operator 140. Although not shown, the surgery support system 100 further includes a mechanism (e.g. a drive arm connected mechanically to the imaging and irradiating device 200 or casters of a pedestal on which a set of the surgery support system 100 is mounted) for changing a position at which the imaging and irradiating device 200 is located.

The imaging and irracfl ating device 200 is a device integrally accommodating an imaging means and an irradiating means. The imaging and irradiating device 200 includes an infrared camera 210, a dichroic mirror 211, and a projector 220. The imaging and irradiating device 200 detects infrared fluorescent light 223 radiating from the patient 120 lying on the operating table 110. Visible irradiation light 222 projected from the projector 220 is then irradiated on a region of the affected part 130 indicated by the detected infrared fluorescent light 223. For more proper detection of the infrared fluorescent light 223 and for more proper irradiation of the visible irradiation light 222, the imaging and irradiating device 200 may be preferably located right above the patient 120 lying on the operating table 110.

The projection controller 300 is a device that performs overall control of units composing the surgery support system 100. The projection controller 300 is connected electrically to the infrared camera 210, the projector 220, the infrared excitation light source 230, and the memory 240 to control those. The projection controller 300 is composed of a CPU or an MPU, for example, and executes predetermined programs to achieve functions thereof. The functions of the projection controller 300 may be implemented by a dedicatedly designed electronic circuit.

The memory 240 is a storage medium which the projection controller 300 properly accesses when executing an arithmetic operation.

The infrared excitation light source 230 is a light source irradiating infrared excitation light 231 of at least approx. 800 nm that is an ICC excitation wavelength. The infrared excitation light source 230 can switch ON/OFF of irradiation of the infrared excitation light 231 in response to a control signal from the projection controller 300. The infrared excitation light source 230 may be preferably located right above the patient 120 lying on the operating bed 110 in order to reduce uneven irradiation of the infrared excitation light 231.

The display controller 150 is connected electrically to the display 160 and the mouse 170. The display 160 can display a menu for performing various settings related to projecting actions of the projection controller 300. The operator 140 grips and operates the mouse 170 while looking at the menu displayed on the display 160 so as to perform various settings related to the projecting actions of the projection controller 300. More specifically, settings can be performed for switching of colors of projection light which are projected on the ICG light-emitting region (affected part 130) and of the number of grayscale level thereof and for switching of colors of projection light which are projected on a periphery (background) of the ICG light-emitting region and on a contour thereof. When receiving a setting operation from the operator 140, the display controller 150 notifies the projection controller 300 of the setting to reflect the setting. This causes the projection controller 300 to perform a projecting action in accordance with the settings set by the operator 140. The display 160 can be of any of various types such as a liquid crystal display type and an organic EL type. The mouse 170 is an example of the operating means and may be replaced by another operating means such as a touch panel or a keyboard.

Next, configurations included in the imaging and irradiating device 200 will be described.

The infrared camera 210 is a camera having a spectral sensitivity characteristic in an infrared region. In the surgery support system 100 according to the present disclosure, it is necessary to detect the infrared fluorescent light 223 of approx. 850 nm emitted from ICG. For this reason, the infrared camera 210 has a spectral sensitivity characteristic in the infrared region including at least 850 nm. To avoid reception of light other than the infrared fluorescent light 223 emitted from ICG, a bandpass filter allowing only light of approx. 850 nm in wavelength to pass therethrough may be di sposed in front of the infrared camera 210. The infrared camera 210 transmits an infrared image captured by imaging to the projection controller 300.

The projector 220 is a projection device that irradiates visible light in response to a control signal from the projection controller 300. The projector 220 can use light of any width of wavelength (color) as long as it is in a visible light region visually recognizable by human beings. The projector 220 is configured to be able to switch irradiation of light of plural wavelengths (colors) in accordance with a control signal from the projection controller 300. The projector 220 irradiates the visible irradiation light 222 toward the dichroic mirror 211.

The dichroic mirror 211 is arranged facing the infrared camera 210 and the projector 220. The dichroic mirror 211 is an optical element that has functions of reflecting light of a specific wavelength but of transmitting light of the other wavelengths. In the present disclosure, a projecting outlet of the projector 220 is arranged directed to the dichroic mirror 211 disposed alongside the projector 220 in a horizontal direction, while the infrared camera 210 is arranged vertically above the dichroic mirror 211. The dichroic mirror 211 has optical characteristics of reflecting the visible irradiation light 222 irradiated from the projector 220 and of transmitting the infrared fluorescent light 223 traveling toward an imaging surface of the infrared camera 210. As depicted in FIG. 1, the visible irradiation light 222 reflected on the dichroic mirror 211 and the infrared fluorescent light 223 incident on the imaging surface of the infrared camera 210 have the identical optical path. It is thereby possible to enhance accuracy of irradiation of the visible irradiation light 222 onto a region (affected part 130) emitting the infrared fluorescent light 223.

In the above, the infrared camera 210 is an example of a detector of the present disclosure. The projector 220 is an example of a projecting unit that performs projection using visible light of the present disclosure. The combination of the display controller 150 and the projection controller 300 is an example of a control unit of the present disclosure. The surgery support system 100 is an example of a visible light projection device of the present disclosure.

In the example shown in FIG. 1, the display controller 150 and the projection controller 300 are exemplified as being separate hardware configurations. The present disclosure is not limited thereto. For example, the display controller 150 and the projection controller 300 may be foLmed as an integrated hardware configuration.

3. Image Processing by Projection Controller

Figure 2:
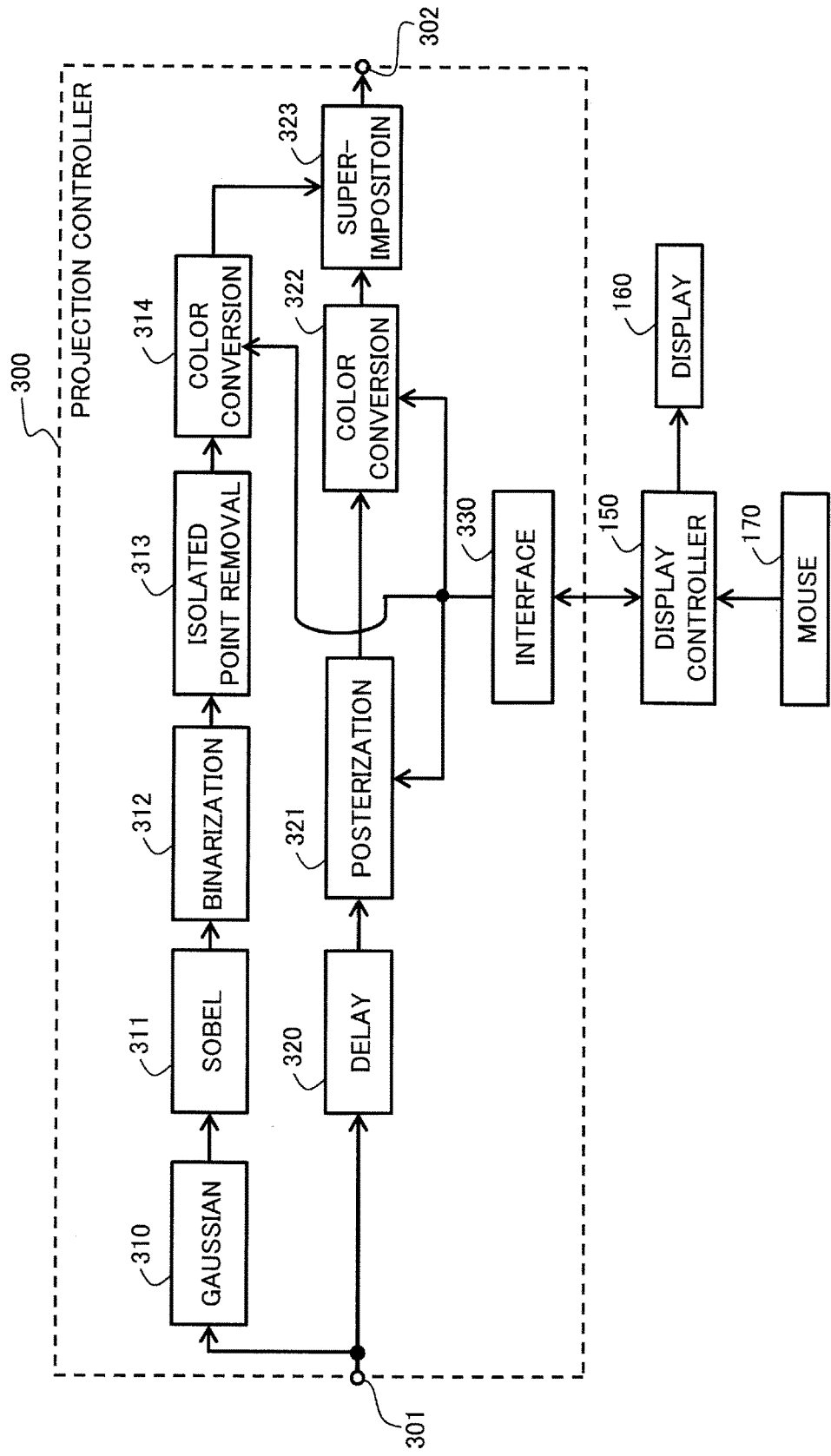
FIG. 2 is a diagram explaining a configuration related to image processing of a projection control device.

Succeedingly, details of image processing by the projection controller 300 will be described. FIG. 2 is a diagram explaining a configuration related to the image processing of the projection controller 300.

As depicted in FIG. 2, the projection controller 300 has functions of a Gaussian filter 310, a Sobel filter 311, a binarization process 312, an isolated point removal process 313, a color conversion process 314, a delay process 320, a posterization process 321, a color conversion process 322, and a superimposition process 323. These functions may be implemented by hardware or may be implemented by software. The projection controller 300 is connected via an interface 330 to the display controller 150.

Details of the functions possessed by the projection controller 300 will be described.

An infrared image captured and generated by the infrared camera 210 is imported via an input 301 into the projection controller 300. The infrared image imported from the input 301 is sent to the Gaussian filter 310 and the delay process 320.

As preprocessing of an edge detection of a region from which ICG emits the infrared fluorescent light 223, the Gaussian filter 310 removes noise components contained in the infrared image generated by the infrared camera 210. A coordinate of a target pixel in the infrared image, for which noise components are to be removed is represented by $(X, Y)$, and a signal level at the coordinate $(X, Y)$ is represented by $LV(X, Y)$. At this time, a matrix S1 indicating signal levels of the target pixel to remove the noise components and of eight pixels adjacent to the target pixel is a matrix expressed by the following equation (1).

$$S1 = \begin{pmatrix} LV(X-1, Y-1) & LV(X, Y-1) & LV(X+1, Y-1) \\ LV(X-1, Y) & LV(X, Y) & LV(X+1, Y) \\ LV(X-1, Y+1) & LV(X, Y+1) & LV(X+1, Y+1) \end{pmatrix}$$ [Equation (1)]

The Gaussian filter 310 performs smoothing of the matrix S1, based on a filter coefficient (Gaussian filter) G expressed by Equation (2). Specifically, as shown in Equation (3), the signal level S1 is multiplied by the filter coefficient G so that noise components contained in the image can be removed.

$$G = \begin{pmatrix} 1 & 2 & 1 \\ 2 & 4 & 2 \\ 1 & 2 & 1 \end{pmatrix}$$ [Equation (2)]

$$G*S1 = \{1 \times LV(X-1, Y-1) + \\ 2 \times LV(X, Y-1) + 1 \times LV(X+1, Y-1) + \\ 2 \times LV(X-1, Y) + 4 \times LV(X, Y) + \\ 2 \times LV(X+1, Y) + 1 \times LV(X-1, Y+1) + \\ 2 \times LV(X, Y+1) + 1 \times LV(X+1, Y+1)\}/16$$ [Equation (3)]

The Sobel filter 311 detects a pixel having a larger difference in relative brightness with respect to its peripheral pixels in pixels composing the infrared image output from the Gaussian filter 310. Specifically, the Sobel filter 311 detects an edge portion of the infrared image. It is noted that $(X, Y)$ is a coordinate of a target pixel for the edge detection effected by the Sobel filter 311 and EG $(X, Y)$ is a signal level at the coordinate $(X, Y)$. At this time, signal levels S2 of the target pixel for the edge detection and its adjacent 8 pixels are represented as a matrix expressed by the following Equation (4).

$$S2 = \begin{pmatrix} EG(X-1, Y-1) & EG(X, Y-1) & EG(X+1, Y-1) \\ EG(X-1, Y) & EG(X, Y) & EG(X+1, Y) \\ EG(X-1, Y+1) & EG(X, Y+1) & EG(X+1, Y+1) \end{pmatrix}$$ [Equation (4)]

The Sobel filter 311 performs an edge detection process for horizontal component, based on the matrix S2 and a filter coefficient (horizontal Sobel filter) SH expressed by the Equation (5). More specifically, as expressed by the Equation (6), the filter coefficient SH and the signal level S2 are multiplied together to take an absolute value thereof, to thereby perform the edge detection process for horizontal component of a target pixel for edge detection. In this manner, the Sobel filter 311 performs the edge detection processing for horizontal component, for each of pixels composing the infrared image.

$$SH = \begin{pmatrix} -1 & 0 & 1 \\ -2 & 0 & 2 \\ -1 & 0 & 1 \end{pmatrix}$$ [Equation (5)]

$$SH*S2 = \text{Absolute Value}$$ [Equation (6)]
$$\{-1 \times EG(X-1, Y-1) + 0 \times EG(X, Y-1) + \\ 1 \times EG(X+1, Y-1) - 2 \times EG(X-1, Y) + \\ 0 \times EG(X, Y) + 2 \times EG(X+1, Y) - \\ 1 \times EG(X-1, Y+1) + \\ 0 \times EG(X, Y+1) + 1 \times EG(X+1, Y+1)\}$$

Similarly, the Sobel filter 311 performs an edge detection process for vertical component, based on the matrix S2 and a filter coefficient (vertical Sobel filter) SP expressed by Equation (7). More specifically, as expressed by Equation (6), the filter coefficient SP and the signal level S2 are multiplied together to take an absolute value thereof, to thereby perform the edge detection process for vertical component of a target pixel for edge detection. In this manner, the Sobel filter 311 performs the edge detection for vertical component, for each of pixels composing the infrared image.

$$SP = \begin{pmatrix} -1 & -2 & -1 \\ 0 & 0 & 0 \\ 1 & 2 & 1 \end{pmatrix}$$ [Equation (7)]

$$SH*S2 = \text{Absolute Value}$$ [Equation (8)]
$$\{-1 \times EG(X-1, Y-1) - 2 \times EG(X, Y-1) - \\ 1 \times EG(X+1, Y-1) + 0 \times EG(X-1, Y) + \\ 0 \times EG(X, Y) + 0 \times EG(X+1, Y) + \\ 1 \times EG(X-1, Y+1) + \\ 2 \times EG(X, Y+1) + 1 \times EG(X+1, Y+1)\}$$

Succeedingly, the Sobel filter 311 performs comparison between the found horizontal component and vertical component, for each of pixels composing the infrared image. When the horizontal component is equal to or greater than the vertical component, the Sobel filter 311 determines an edge component of the target pixel based on Equation (9). On the other hand, when the horizontal component is smaller than the vertical component, the Sobel filter 311 determines an edge component of the target pixel based on Equation (10). In this manner, the Sobel filter 311 determines the edge component for each of pixels composing the infrared image.

Edge component=horizontal component+vertical component/2   [Equation (9)]

Edge component=vertical component+horizontal component/2   [Equation (10)]

As a result, the edge component containing a diagonal direction can simply be calculated.

The binarization process 312 binarizes the edge component of each of pixels composing the infrared image, output from the Sobel filter 311. The pixel with a small edge component is equivalent to a noise component or a minute texture component, and therefore an enhancement process is not required for it. Accordingly, the binarization process 312 sets a predetermined threshold value to the edge component for binarization and performs binarization with the predetermined threshold value so as to selectively extract a contour portion of the ICG light-emitting region for each of pixels composing the infrared image. The threshold value for binarization may be selectable by the operator 140 so that the degree of detection of the contour portion can be adjusted.

The isolated point removal process 313 performs isolated point removal for binary information of the infrared image output by the binarization process 312. The isolated point removal process 313 is a process of converting a white pixel existing in isolation among black pixels to a black pixel, since it determines the white pixel existing in isolation among black pixels as a granular noise component. Further, the isolated point removal process 313 converts a black pixel existing in isolation among white pixels to a white pixel, since it determines the black pixel existing in isolation among white pixels as a granular noise component. There may be a case where the noise components cannot sufficiently be removed merely by performing the binarization process of the edge component by the binarization process 312 when the surface condition of the affected part 130 on which an image is projected by the imaging and irradiating device 200 is not good, such as the affected part 130 which is peeled off from other organs when the affected part 130 adheres to the other organs. For this reason, the isolated point removal process 313 performs isolated point removal after the binarization process of the edge component. This enables fine granular noise components to be removed while leaving a major part of the contour portion of the ICG light-emitting region. The level of the noise removal effect by the isolated point removal process 313 may be selectable by the operator 140. At this time, for example, two options may be prepared, i.e., a case where determination is made from four pixels up, down, left, and right of a target pixel (noise removal effect: small) and a case where determination is made from eight pixels containing diagonal directions (noise removal effect: large). Further, it may be possible for the operator 140 to adjust ON/OFF of the isolated point removal process 313depending on the state of the affected part 130, various cases, etc.

The color conversion process 314 performs color conversion of an edge component (contour portion of the ICG light-emitting region) output from the isolated point removal process 313, in order to increase the visibility of the visible light projection on the ICG light-emitting region. The operator 140 can select a color of the contour portion of the ICG light-emitting region from variations lined up as options. The color conversion process 314 converts the color of the edge component (contour portion of the ICG light-emitting region) to a color selected by the operator 140.

The delay process 320 acquires, from the input 301, an infrared image captured and generated by the infrared camera 210. The delay process 320 applies a delay process with predetermined lines to the acquired infrared image. More specifically, the delay process 320 delays the infrared image of the same content imported from the input 301 to coincide, at the time of superimposition in the superimposition process 323, the timing of the edge detection processed along a path of the Gaussian filter 310, the Sober filter 311, the binarization process 312, the isolated point removal process 313, and the color conversion process 314 with the timing of the image processed along a path of the posterization process 321 and the color conversion process 322. As a result, a proper superimposed image can be obtained in the superimposition process 323. Although in the example shown in FIG. 2, the delay process 320 is arranged as preprocessing of the posterization process 321 and the color conversion process 322, the position of the delay process 320 is not limited to this. As long as the timings can coincide in the superimposition process, the delay process 320 may be arranged between the posterization process 321 and the color conversion process 322 or may be arranged posterior to the color conversion process 322.

The posterization process 321 performs posterization processing for the infrared image output by the delay process 320. For example, it is assumed that the original infrared image has 256 grayscale levels. The posterization process 321 converts grayscale level of the original infrared image to a grayscale level set by the operator 140, such as 2, 4, 8, or 256 levels.

When 2 levels are set, the posterization process 321 sets the threshold value to 127. For a pixel having a grayscale level from 0 to 127 in the infrared image, a value of the pixel is converted to 0. On the other hand, for a pixel having a grayscale level from 128 to 255 in the infrared image, a value of the pixel is converted to 255. As a result, the posterization process 321 generates a 2 grayscale level infrared image.

When 4 levels are set, the posterization process 321 sets three threshold values of 63, 127, and 191. For a pixel having a grayscale level from 0 to 63 in the infrared image, a value of the pixel is converted to 0. For a pixel having a grayscale level from 64 to 127 in the infrared image, a value of the pixel is converted to 85. For a pixel having a grayscale level of 128 to 191 in the infrared image, the value of the piexel is converted to 170. For a pixel having a grayscale of 192 to 255 in the infrared image, the value of the pixel is converted to 255. As a result, the posterization process 321 generates a 4 level grayscale infrared image.

When 8 grayscale levels are set, the posterization process 321 sets seven threshold values of 31, 63, 95, 127, 159, 191, and 223. For a pixel having a grayscale level from 0 to 31 in the infrared image, a values of the pixel is converted to 0. For a pixel having a grayscale level from 32 to 63 in the infrared image, a values of the pixel is converted to 36. For a pixel having a grayscale level from 64 to 95 in the infrared image, a values of the pixel is converted to 73. For a pixel having a grayscale level of 96 to 127 in the infrared image, a values of the pixel is converted to 109. For a pixel having a grayscale level from 128 to 159 in the infrared image, a values of the pixel is converted to 146. For a pixel having a grayscale level from 160 to 191 in the infrared image, a values of the pixel is converted to 182. For a pixel having a grayscale level from 192 to 223 in the infrared image, a values of the pixel is converted to 219. For a pixel having a grayscale level of 224 to 255 in the infrared image, a values of the pixel is converted to 255. As a result, the posterization process 321 generates an 8-grayscale level infrared image.

When 256 grayscale levels are set, the posterization process 321 outputs the grayscale levels of the original infrared image as they are. Specifically, 256-grayscale level infrared image is output.

In this manner, the operator 140 can set the optimum number of grayscale levels depending on the state of the affected part 130, various cases, etc.

The number of grayscale levels selectable by the operator 140 may include the same number as the number of grayscale levels of the original image.

The color conversion process 322 performs color conversion of the infrared image (a surface portion of the ICG light-emitting region and a background surrounding the surface portion) output from the posterization process 321, in order to increase visibility of the visible light projection on the ICG light-emitting region. The operator 14 can select one color of the surface portion of the ICG light-emitting region from plural color variations lined up as options. Similarly, the operator 14 can select one color of the background surrounding the surface portion of the ICG light-emitting region from plural color variations lined up as options. In this embodiment, either one of black and white can be selected as the background color. Particularly, in the case of selecting white as the background color, it is possible to secure both the brightness of the surgical field required for surgery and the visibility of the ICG light-emitting region, without turning on a shadowless light. The color conversion process 322 converts the color of the infrared image (the surface portion of the ICG light-emitting region and the background surrounding the surface portion) to a color selected by the operator 140.

The superimposition process 323 superimposes the color-converted edge component (the contour portion of the ICG light-emitting region) output from the color conversion process 314 on the color-converted infrared image (the surface portion of the ICG light-emitting region and the background surrounding the surface portion) output from the color conversion process 322. As described earlier, the infrared image and the edge component to be superimposed are based on the infrared image captured by the infrared camera 210 at the same timing. The superimposition process 323 provides projection control data based on the superimposed infrared image, via an output 302, to the projector 220. As a result, the projector 220 can project visible light onto the surface portion of the ICG light-emitting region, the background surrounding the surface portion, and the contour portion.

The interface 330 is connected electrically to the display controller 150. The interface 330 then converts a control signal for a setting operation which is sent from the display controller 150, to a signal available in the projection controller 300. Specifically, the interface 330 using a USB/IIC converter converts various set values controlled by the display controller 150 to IIC signals available in the projection controller 300. The interface 330 then provides the converted signals to the posterization process 321, the color conversion process 314, and the color conversion process 322. This enables the various setting operations by the operator 140 to be reflected.

4. Image Processing by Projection Control Device

Succeedingly, description will be given of a screen displayed on the display 160 when the operator 140 performs various setting operations.

Figure 3A:
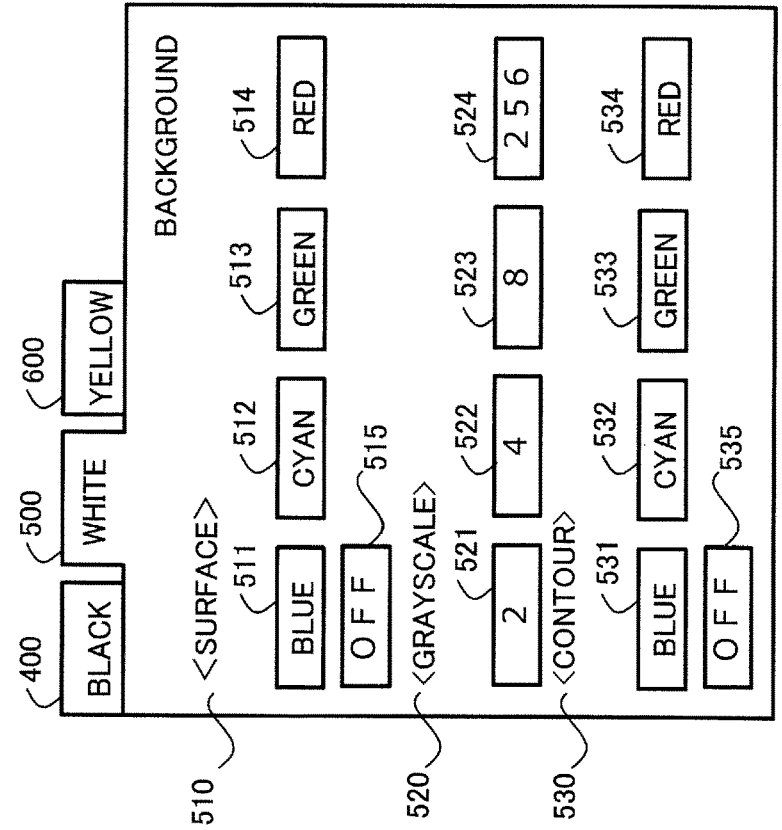
FIGS. 3A and 3B are diagrams explaining images displayed when an operator 140 performs various setting operations.
Figure 3B:
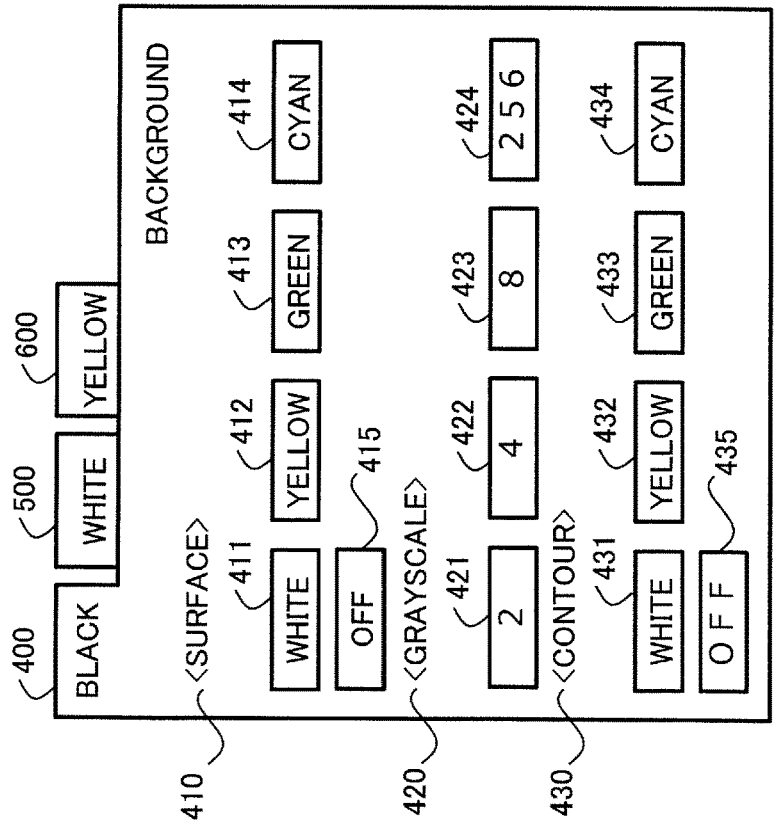
Figure 4A:
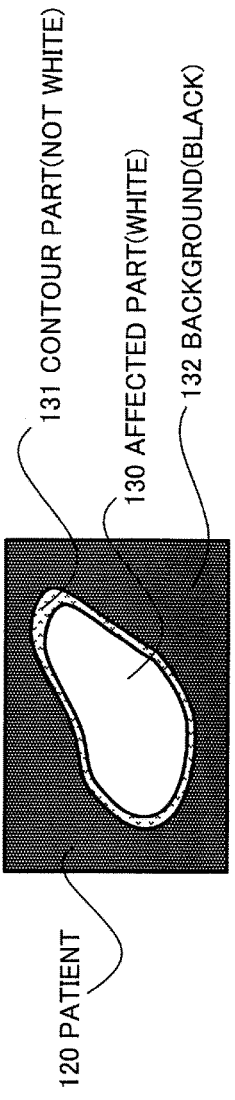
FIGS. 4A-4D are image views each depicting a projection video in a case where the grayscale level is limited to 2 levels with a black background color.
Figure 4B:
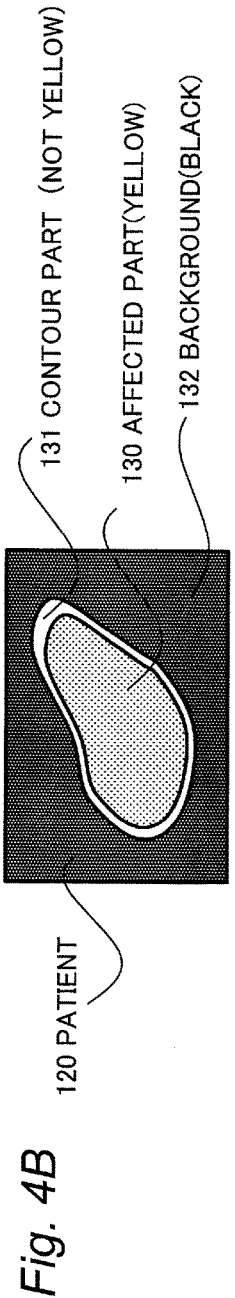
Figure 4C:
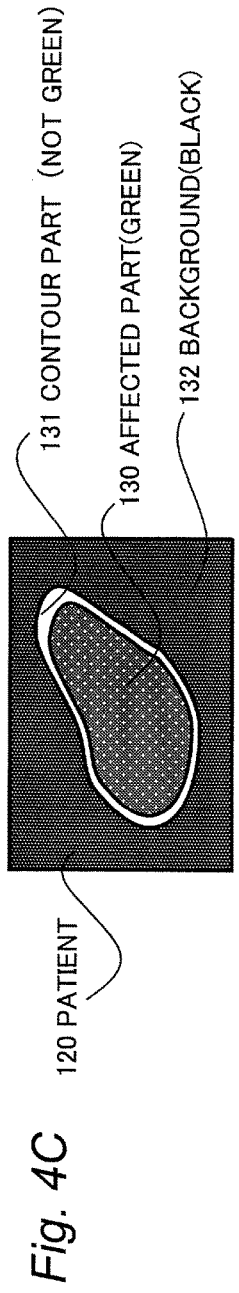
Figure 4D:
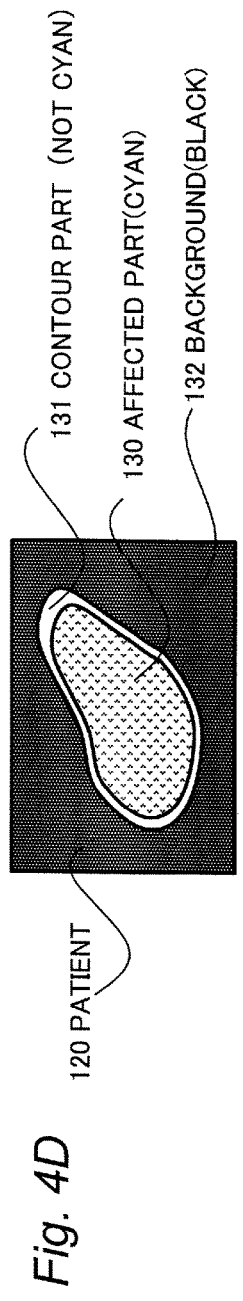

FIGS. 3A and 3B are diagrams explaining screens to be displayed when the operator 140 performs various setting operations.

As shown in FIGS. 3A and 3B, windows segmented by plural tabs is displayed on the display 160. Each of the plural tabs indicates a color of the background surrounding the surface portion of the ICG light-emitting region. In the examples shown in FIGS. 3A and 3B, each of the plural tabs indicates a black background tab 400, a white background tab 500, or a yellow background tab 600. The operator 140 clicks on one of the tabs using the mouse 170 to select one of the background colors. When either one of the tabs is selected, the display 160 displays a selection itemmenu related to the selected tab on the front of that related to the other tabs.

Examples of of the menus shown in FIGS. 3A and 3B will be described. Referring first to FIG. 3A, description will be given of a case where black is selected as the color of the background surrounding the surface portion of the ICG light-emitting region. FIG. 3A shows a menu to be shown when black is selected as the color of the background surrounding the surface portion of the ICG light-emitting region.

When the operator 140 clicks on the black background tab 400 using the mouse 170, the display 160 displays a menu as shown in FIG. 3A. The menu has buttons arrayed to select, when the black background is selected, the color (item 410) projected onto the surface portion of the ICG light-emitting region, the number of grayscale levels (item 420) of projection on the surface portion of the ICG light-emitting region, and the color (item 430) of light projected onto the contour portion (boundary between the surface portion and the background) of the ICG light-emitting region. The items 410, 420, and 430 will be described in order.

First the item 410 is described below. For selection of the color (item 410) projected onto the surface portion of the ICG light-emitting region, a white button 411, a yellow button 412, a green button 413, a cyan button 414, and an OFF button 415 are arranged and displayed.

When the operator 140 selects one of the buttons of the item 410, the display controller 150 notifies the projection controller 300 (the color conversion process 322) of the selection. As a result, the projection controller 300 (the color conversion process 322) performs color conversion of the infrared image by the color selected by the operator 140. The projection controller 300 then causes the projector 220 to perform projection on the surface portion with the color selected by the operator 140. For example, when the operator 140 selects the white button 411, the color of projection on the surface portion turns to white. Similarly, when the operator 140 selects the yellow button 412, the color turns to yellow. When the operator 140 selects the green button 413, the color turns to green. When the operator 140 selects the cyan button 414, the color turns to cyan. When the operator 140 selects the OFF button 415, projection on the ICG light-emitting region is turned off . In other words, when the OFF button 415 is selected, the ICG light-emitting region turns to black that is the same as the background color.

Next, the item 420 is described below. Irrespective of whether the black background is selected, a 2-grayscale level button 421, a 4-grayscale level button 422, an 8-grayscale level button 423, and a 256-grayscale level button 424 are arranged and displayed to select the number of grayscale level of projection on the surface portion of the ICG light-emitting region.

When the operator 140 selects one of the buttons of the item 420, the display controller 150 notifies the projection controller 300 (the posterization process 321) of the selection. As a result, the projection controller 300 (the posterization process 321) performs posterization processing of the infrared image with the number of grayscale level selected by the operator 140. The projection controller 300 then causes the projector 220 to perform projection on the surface portion with the number of grayscale level selected by the operator 140. For example, when the operator selects the 2-grayscale level button 421, projection on the surface portion turns to 2 grayscale level. When the operator selects the 4-grayscale level button 422, projection on the surface portion turns to 4 grayscale level. When the operator selects the 8-grayscale level button 423, projection on the surface portion turns to 8 grayscale level. When the operator selects the 256-grayscale level button 424, projection on the surface portion turns to 256 grayscale level (no limited grayscale level).

Lastly, the item 430 is described. For selection of the color (item 430) projected on the contour portion of the ICG light-emitting region, a white button 431, a yellow button 432, a green button 433, a cyan button 434, and an OFF button 435 are arranged and displayed. When the operator 140 selects one of the buttons of the item 430, the display controller 150 notifies the projection controller 300 (the color conversion process 314) of the selection. As a result, the projection controller 300 (the color conversion process 314) performs color conversion of the infrared image with the color selected by the operator 140. The projection controller 300 then causes the projector 220 to perform projection on the contour portion with the color selected by the operator 140. The operation of switching the projection color when the operator 140 selects one of the white button 431, the yellow button 432, the green button 433, the cyan button 434, and the OFF button 435 is similar to the case of the item 410 for the surface portion, and therefore detailed description thereof is omitted herein.

Succeedingly, referring to FIG. 3B, description is given of a case where white is selected as the color of the background surrounding the surface portion of the ICG light-emitting region. FIG. 3B shows a menu displayed when white is selected as the color of the background surrounding the surface portion of the ICG light-emitting region.

When the operator 140 clicks on the white background tab 500 using the mouse 170, the display 160 displays a menu as shown in FIG. 3B. The menu has buttons arrayed to select, when the white background is selected, the color (item 510) projected onto the surface portion of the ICG light-emitting region, the number of grayscales (item 520) of projection on the surface portion of the ICG light-emitting region, and the color (item 530) projected onto the contour portion (boundary between the surface portion and the background) of the ICG light-emitting region. The items 510, 520, and 530 are described in order.

First the item 510 is described. For selection of the color (item 510) projected onto the surface portion of the ICG light-emitting region, a blue button 511, a cyan button 512, a green button 513, a red button 514, and an OFF button 515 are arranged and displayed. The switching operation of the projection color when the operator 140 selects one of the buttons of the item 510 is similar to the case of selecting one of the buttons of the item 410 for the black background, and therefore detailed description thereof is omitted herein.

Next, the item 520 is described. Irrespective of whether the white background is selected, a 2-grayscale level button 521, a 4-grayscale level button 522, an 8-grayscale level button 523, and a 256-grayscale level button 524 are arranged and displayed in order to select the number of grayscale level of projection on the surface portion of the ICG light-emitting region. The switching operation of the number of grayscale level when the operator 140 selects one of the buttons of the item 520 is similar to the case of selecting one of the buttons of the item 420 for the black background, and therefore detailed description thereof is omitted herein.

Lastly, the item 530 is described. For selection of the color (item 530) projected on the contour portion of the ICG light-emitting region, a blue button 531, a cyan button 532, a green button 533, a red button 534, and an OFF button 535 are arranged and displayed. The switching operation of the projection color when the operator 140 selects one of the buttons of the item 530 is similar to the case of selecting one of the buttons of the item 430 for the black background, and therefore detailed description thereof is omitted herein.

As shown in FIGS. 3A and 3B, the surgery support system 100 limits the selectable colors of the ICG light-emitting region and of the edge portion, depending on the color of the background surrounding the surface portion of the ICG light-emitting region. In other words, the options of color selectable as the color of the surface portion and the contour portion differ depending on the selected background color. Specifically, the options (white, yellow, green, cyan) of color selectable as the color of the surface portion and the contour portion when the black background is selected is made different from the options (blue, cyan, green, red) of color selectable as the color of the surface portion and the contour portion when the white background is selected. Although detailed description is omitted, also in the case where the yellow background tab 600 is clicked on to select the yellow background, the options of color selectable as the color of the surface portion and the contour portion differ from the case of selecting the black background or the white background. In consequence, the operator 140 can rapidly select proper colors of the surface portion and the contour portion against the background color.

When the color of light projected on the surface portion of the ICG light-emitting region is the same as the color of light projected on the contour portion (boundary between the surface portion and the background) irrespective of the background color, the surface portion and the contour portion of the ICG light-emitting region become indistinguishable from each other. For this reason, the same projection color may not be selected to the surface portion and the contour portion of the ICG light-emitting region. For example, when the yellow button 412 is selected in the item 410 related to the color selection of the surface portion to turn the color of projection on the surface portion of the ICG light-emitting region to yellow, the yellow button 432 may automatically be prevented from being pressed in the item 420 related to the color selection of the contour portion. However as an exception, the OFF buttons 415 and 435 may be permitted to be pressed at the same time since the OFF buttons 415 and 435 are provided to turn off the projection on the surface portion and the contour portion. Hence, the whole screen projected by the projector 220 may be permitted to compulsorily be a black screen. Although the case of the black background has been described in the above explanation, the same applies to the case of the white background.

Detailed description is given of the significance of limiting the selectable color of the surface portion and the contour portion depending on the color of the background surrounding the surface portion of the ICG light-emitting region.

It is generally known that the most important color factor to enhance the visibility for the difference in color of the projection light is "difference in value" and then "difference in saturation" and "difference in hue" in the descending order. For example, in the case of employing black with the lowest value as the background color, the color maximizing the lightness difference can be white having the highest value among achromatic colors and yellow having the highest value among chromatic colors. Accordingly, in order to maximize the visibility when the background color is black, the color of the projection light on the surface portion of the ICG light-emitting region may be white or yellow. A combination of black and yellow is employed, for example, in a traffic sign such as "warning sign" calling driver's attention or a label affixed to products according to "Product Liability (PL) Act".

On the other hand, in the case of employing white with the highest value as the background color, the color maximizing the difference in value can be black having the lowest value among achromatic colors and blue having the lowest value among chromatic colors. Accordingly, black or blue may be selected as the color of the projection light on the surface portion of the ICG light-emitting region in order to maximize the visibility when the background color is white. However, in the case of combination of white background color and black projection color on the surface portion of the ICG light-emitting region, a black portion (portion having a weak ICG emission intensity) in the infrared image captured by the infrared camera 210 is projected as being white, whereas a white portion (portion having a strong ICG emission intensity) in the infrared image captured by the infrared camera 210 is projected as being black. At this time, the operator 140 may mistakenly recognize the ICG emission intensity distribution projected on the affected part 130, and therefore such a color combination should desirably be avoided. Hence, in the case of using the white background, in order to maximize the visibility without mistakenly recognizing by the operator 140, blue can be selected as the color of projection color on the surface portion of the ICG light-emitting region. A combination of white and blue can be used, for example, in a traffic sign such as "instruction sign" or "guide sign" instantly giving information to the driver.

In the above description, a different projection color can be selected depending on the background color in order to increase the visibility. This may allow selection of a projection color easy to view for a doctor depending on the color of the affected part 130 or a projection color which is less stressful to doctor's eyes. Alternatively, it may allow selection of a projection color different from the color of body fluids arising from the affected part 130, etc. during surgery or a projection color easy to view the surface condition (vasa vasorum or tissue condition of section) of the affected part to be projected.

In the above description, the infrared fluorescent light is detected by combination of the infrared excitation light and ICG. The wavelengths of the excitation light and the fluorescent light to be detected may be any value, such as the other combination than the above, for example, combination of visible excitation light and a reagent may be employed to detect the visible fluorescent light. However, the wavelength of the fluorescent light may preferably differ from the wavelength of projected light.

Information projected on the affected part 130 can be a CT or MRI image, an ultrasonic image, or a 3D simulation image generated based on at least one of those images.

5. Projection Video

Succeedingly, a projection image projected on the patient 120 by the surgery support system 100 is described. FIGS. 4A to 4D are views depicting a projection image in a case where the number of grayscale level is limited to 2 level with a black background color.

When the black background color is selected, in a region (ICG non-light-emitting region) having a weak ICG emission intensity such as a background 132 as shown in FIGS. 4A to 4D, the grayscale is converted to 0, and hence projection light is not projected thereon. On the other hand, in a region having a strong ICG emission intensity, the grayscale is converted to 255, and projection light of a color set in accordance with a projection color selected by the operator 140 is projected thereon, such as the affected part 130 as shown in FIGS. 4A to 4D. Furthermore, the contour portion of the ICG light-emitting region is also irradiated with projection light of a color in accordance with the selected projection color, such as a contour portion 131 as shown in FIGS. 4A to 4D.

FIGS. 5A to 5D are views depicting a projection image projected when the number of grayscale level is limited to 2 with a white background color. When the white background color is selected, the grayscale of RGB are all converted to 255 in a region (ICG non-light-emitting region) having a weak ICG emission intensity such as a background 132 shown in FIGS. 5A to 5D, so that white projection light is projected thereon. On the other hand, in a region having a strong ICG emission intensity, the grayscale of a color of R, G and B which is not influencing a set projection color is converted to 0, and projection light of a color set according to a projection color selected by the operator 140 is projected thereon, such as the affected part 130 shown in FIGS. 5A to 5D. FurtheLmore, the contour portion of the ICG light-emitting region is also irradiated with projection light of a color set according to the selected projection color, such as a contour portion 131 shown in FIGS. 5A to 5D. It is to be noted that in the case of selecting the white background color, when blue is selected as the projection color projected onto the ICG light-emitting region, the visibility is maximized. Furthermore, selection of cyan or green secures a good visibility and less eyestrain. In some cases, color of body fluids may resemble the color other than blue, such as green. In that case, red is selected to avoid misrecognition.

In both cases of setting the black background and setting the white background, the color of projection light projected on the contour portion 131 is made different from the color of projection light projected on the affected part 130 so that the position of the contour portion becomes clear. It is to be noted, however, that the boundary between the ICG light-emitting region and the ICG non-light-emitting region does not necessarily coincide with the contour portion of the ICG light-emitting region. When the number of grayscale levels is limited to 2, the threshold value for determining the grayscale to be 0 or 255 may be changed for adjustment to obtain an optimum projection image. The level of the grayscale may not be limited to 0 and 255.

Figure 6A:
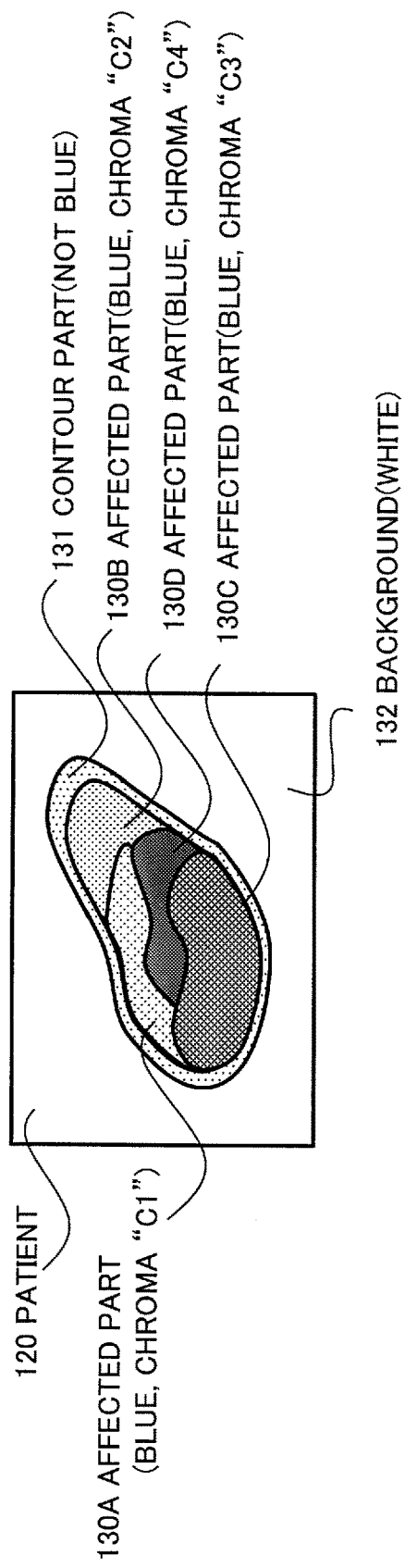
FIGS. 6A and 6B are views each depicting a projection video in a case where the grayscale level is limited to 4 with the white background color.

FIG. 6A is a view showing a projection image projected in a case where the number of grayscale levels is limited to 4 with the white background color. Also in the case of 8 grayscale levels and 256 grayscale levels, a similar projection to the case of 4 grayscale levels can be generated except for the number of grayscale levels. Like affected parts 130A to 130D shown in FIG. 6A, in the case of setting 4-grayscale level, the grayscale is assigned to 4 levels of 0, 85, 170, and 255 in the ascending order of the ICG emission intensity, to project projection light of a color set according to the projection color selected by the operator 140. Furthericiore, the contour portion 131 of the ICG light-emitting region is also irradiated with projection light of a color set according to the selected projection color. It is to be noted, similarly to the case of 2-grayscale level, that the boundary of the projection regions with the respective grayscale levels does not necessarily coincide with the contour portion of the ICG light-emitting region. When the number of grayscale levels is limited to 4, the threshold values for determining the grayscale to be 0, 85, 170, or 255 may be changed for adjustment to obtain an optimum projection image. All the threshold values may separately be set. Alternatively, one threshold value may be set while the other threshold values may be set in conjunction with the one threshold value. The value of the projection grayscale may not be limited to 0, 85, 170, and 255.

The color of projection light for expressing grayscale on the surface portion of the ICG light-emitting region is described in detail below.

There is a trade-off between amount of the information of the ICG emission intensity and visibility, in a projection image projected on the affected part 130. Specifically, as the number of grayscale levels increases, a more delicate change in the ICG emission intensity can be expressed by the projection, but a projection image with less visibility and no sharpness arises due to a reduced difference between the projection colors at the respective grayscales. On the contrary, as the number of grayscale levels decreases, it becomes more difficult to express a delicate change in the ICG emission intensity by projection, but a projection image with high visibility and sharpness is obtained due to an increased difference between the projection colors at the respective grayscales.

Regarding the projection color for grayscale expression, "difference in value" is the important factor to increase the visibility, as described above. For this reason, it is basically desirable that the grayscale be expressed by changing the value. However, when a color with a large difference in lightness from the background color is projected on the surface portion of the ICG light-emitting region, human eyes have visual characteristics called "value contrast" by which a brighter color than the background color looks even brighter while a darker color than the background color looks even darker. When the background color is black, the value of the projection color on the surface portion of the ICG light-emitting region is always greater than the value of the background color. By virtue of the value contrast effect, human eyes feel it brighter than its original brightness so that differences between the projection colors in the respective grayscale levels look more emphasized. Thus, in the case of selecting the black background, projection image can satisfactorily be projected on the surface portion of the ICG light-emitting region with the selected projection color.

On the other hand, in the case where the background color is white, the value of the projection color on the surface portion of the ICG light-emitting region becomes always smaller than the value of the background color. Due to the value contrast effect, human eyes feel it darker than its original brightness so that differences between the projection colors in the respective grayscales become more indistinguishable. Thus, in the case of employing the white background, the grayscale is desirably expressed not by "difference in value" but by "difference in saturation" that is an important element next to "difference in value" in the color visibility.

Figure 6B:
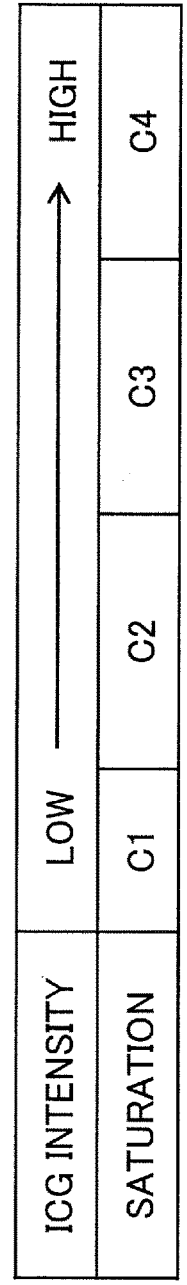

FIG. 6B shows a table depicting the difference in saturation with respect to the ICG emission intensity. In an example shown in FIG. 6B, the grayscale expression is set such that the saturation (C) becomes higher as the ICG emission intensity increases. Specifically, the grayscale expression is set such that as the ICG emission intensity goes from a strong region toward a weak region, the saturation changes through C4, C3, C2, and C1 in this order. Like affected parts 130A to 130D shown in FIG. 6A, in the case of 4-grayscales, the grayscales are assigned to four levels 0, 85, 170, and 255 in the ascending order of the ICG emission intensity and the saturation C1, C2, C3, and C4 are set for the respective grayscales. It is assumed here that the ICG emission intensity increases through the affected parts 130A, 130B, 130C, and 130D in this order. At this time, the imaging and irradiating device 200 performs projection of a projection color (e.g. blue) with the saturation C1 onto the affected part 130A. Projection of a projection color with the saturation C2 is perfoimed onto the affected part 130B. Projection of a projection color with the saturation C3 is performed onto the affected part 130C. Projection of a projection color with the saturation C4 is perfoLmed onto the affected part 130D. This enables projection with the grayscale expression having increased visibility to be performed on the surface portion of the ICG light-emitting region, even in the case of employing white as the background color.

6. Conclusion

As set forth hereinabove, the surgery support system 100 of the present disclosure includes the infrared camera 210 that detects the affected part 130 emitting the infrared fluorescent light 223, the projector 220 that performs projection using visible light on a surgical field including the affected part 130 (ICG light-emitting region) detected by the infrared camera 210, and the projection controller 300 that controls the projector 220 to perform projection with a color selected by the operator 140. When black is selected as a color of visible light projected by the projector 220 onto a region (background) other than the affected part 130 in the surgical field, the projection controller 300 displays, on the display 160, a menu so as to allow a color of visible light projected by the projector 220 to be selected from first options (white, yellow, green, and cyan), to inform the operator 140 of them. On the other hand, when white is selected as a color of visible light projected by the projector 220 onto a region (background) other than the affected part 130 in the surgical field, the projection controller 300 displays, on the display 160, a menu so as to allow a color of visible light projected by the projector 220 to be selected from second options (blue, cyan, green, and red) different from a combination of candidates included in the first options, to inform the operator 140 of them.

This configuration enables the operator 140 to rapidly select proper colors of the surface portion and of the contour portion against the background color.

Further, as described above, in the surgery support system 100 of the present disclosure, the projection controller 300 prohibits selection of a color selected by the operator as a color of visible light projected by the projector 220 onto the surface portion of the affected part 130, from options for a color of visible light projected by the projector 220 onto the contour portion of the affected part 130 (ICG light-emitting region). This enables the doctor to distinguish the affected part 130 (ICG light-emitting region) from the contour portion.

Further, as described above, in the surgery support system 100 of the present disclosure, in the case where the projector 220 performs multi-grayscale color projection onto the affected part (ICG light-emitting region) 130 depending on intensity of the infrared fluorescent light 223 from each of portions composing the affected part 130 detected by the infrared camera 210, the saturation of the color of the visible light projected from the projector 220 is varied depending on the grayscale. This enables video projection performed with the grayscale expression having high visibility, on the surface portion of the ICG light-emitting region. This is effective in particular when the background color is white.

7. Other Embodiments

As described above, the first embodiment is described as an exemplification of the technique disclosed in the present application. However, the technique in this disclosure is not limited thereto and is applicable also to embodiments subjected to proper modifications, replacements, additions, omissions, etc. It is also possible to combine the components described in the first embodiment to make new embodiments. The other embodiments are thus exemplified hereinbelow.

Although the above embodiment describes, as an example, the case where a button fora desired color is selected from the menu displayed on the display 160 using the mouse 170, this disclosure is not limited thereto. Options related to the projection color may be announced from a speaker connected to the projection controller 300. After hearing the announcement, the operator 140 may perfoun a selecting operation by speaking a desired color into a microphone. The operator 140 may naturally perform the selecting operation by speaking a desired color into the microphone while seeing the buttons on the menu displayed on the display 160.

Although the first embodiment describes an application for the surgical use, as an example, this disclosure is not limited thereto. For example, the present disclosure is applicable also to the case where there is a need to carry out a work for an object whose state change cannot visually be confiuried, as in a construction site, a mining site, a building site, or a factory to process materials.

Specifically, instead of the infrared fluorescent light from ICG of the first embodiment, fluorescent materials may be coated on, kneaded in, or poured into a target of which state change cannot visually be confirmed, as in the construction site, the mining site, the building site, or the factory to process materials. Then the target coated, kneaded, or poured with the fluorescent materials may be imaged by the infrared camera 210, and may be projected visible light thereon. Alternatively, instead of detecting emission of light, a heating portion may be detected by a thermal sensor and visible light may be projected on the detected heating portion. In this case, far-infrared light emitted from the heating portion is also an example of the non-visible light in the present disclosure.

As described above, the embodiments have been described as exemplifications of the technique in the present disclosure. To this end, the accompanying drawings and detailed description have been provided.

Accordingly, the components described in the accompanying drawings and detailed description can include not only components essential to solve the problem but also components unessential to solve the problem, for the purpose of merely exemplifying the above technique. Hence, those unessential components should not directly be construed as being essential from the fact that those unessential components are described in the accompanying drawings and detailed description.

Since the above embodiments are for exemplifying the technique in this disclosure, various modifications, replacements, additions, omissions can be made without departing from the scope of claims and equivalents thereof.

INDUSTRIAL APPLICABILITY

The projection system in this disclosure is applicable, without being limited to the surgical use, to the case of performing a work for an object whose state change cannot visually be confirmed, as in the construction site, the mining site, the building site, or the factory to process materials.

The invention claimed is:

1. A visible light projection device for aiding a surgery comprising:
   a user interface configured to provide information for setting of a color of visible light, and configured to perform the setting of the color of visible light by an operator
   detector configured to detect a first region emitting non-visible light;
   a projector configured to project light on a patient and further configured to perform, based on a control signal, projection using visible light onto a second region including the first region detected by the detector, the control signal being made based on the detected first region; and
   a controller configured to control the projector to perform projection during the surgery with a color selected by an operator, wherein
   when a first color is selected through the user interface, as a color of visible light projected by the projector onto a region other than the first region within the second region, the controller configured to control the user interface to provide first options configured to allow a color of visible light projected onto the first region by the projector to be selected from the first options, and
   when a second color different from the first color is selected through the user interface, as a color of visible light projected by the projector onto a region other than the first region within the second region, the controller controls the user interface to provide second options different from a combination of candidates included in the first options configured to allow a color of visible light projected onto the first region by the projector to be selectable from the second options.

2. The visible light projection device of claim 1, wherein the controller prohibits selection of a color selected by the operator as a color of visible light projected onto the first region by the projector, from options of the color of visible light projected onto a contour portion of the first region by the projector.

3. The visible light projection device of claim 1, wherein when making the projector perform projection onto the first region using color visible light with multi-grayscale levels according to an intensity of non-visible light from portions composing the first region detected by the detector, the controller varies saturation of the color of visible light projected by the projector, according to a grayscale of the visible light.

4. The visible light projection device of claim 2, wherein when making the projector perform projection onto the first region using color visible light with multi-grayscale levels according to an intensity of non-visible light from portions composing the first region detected by the detector, the controller varies saturation of the color of visible light projected by the projector, according to a grayscale of the visible light.

* * * * *